United States Patent [19]
Schmidt

[11] Patent Number: 6,077,529
[45] Date of Patent: *Jun. 20, 2000

[54] ACTIVE INGREDIENT SYSTEM AND METHOD OF MANUFACTURE THEREOF FOR TRANSFER OF LIPOPHILIC AND AMPHIPHILIC COMPONENTS TO TARGET STRUCTURES

[76] Inventor: Karl Heinz Schmidt, 7413 Gomaringen, Aussere Weiler Strasse 12, Germany

[*] Notice: This patent is subject to a terminal disclaimer.

[21] Appl. No.: 07/744,308

[22] Filed: Aug. 13, 1991

Related U.S. Application Data

[63] Continuation-in-part of application No. 07/347,026, May 4, 1989, abandoned.

[30] Foreign Application Priority Data

May 6, 1988 [DE] Germany ............................... 38 15 473

[51] Int. Cl.$^7$ .................................................. A61K 9/127
[52] U.S. Cl. ........................... 424/450; 424/401; 424/43; 424/44; 424/45; 514/78; 514/169; 514/458; 514/725; 514/937
[58] Field of Search ...................................... 424/401, 450, 424/417, 43–45; 436/829; 514/2, 8, 21, 78, 169, 937, 938, 943, 458, 725; 530/388.25

[56] References Cited

U.S. PATENT DOCUMENTS

| | | | |
|---|---|---|---|
| 4,812,314 | 3/1989 | Barenholz et al. | 424/422 |
| 5,128,318 | 7/1992 | Levine et al. | 514/21 |

FOREIGN PATENT DOCUMENTS

WO 8504880 of 1984 WIPO .

OTHER PUBLICATIONS

Brown, Chemistry and Phy. of Lipids 38, 1985, p. 79.
Williams BBA 875 (1986) p. 183.
Brown et al Chemistry & Phys. of Lipids 38, (1985) p. 79. German Search Report, citing reference: Chemistry and Physics of Lipids, 38, 1985, Elsevier Scientific Publishers Ireland Ltd., (S. (page) 79); along with additional pages listed below:

1. Phosphatidylinositol Transfer Proteins: Structure, Catalytic Activity, and Physiological Function, p. 3.

2. Phospholipid Transfer Proteins From Lung, Properties and Possible Physiological Functions, p. 17.

3. The Lipid Binding Site of the Phosphatidylcholine Transfer Protein from Bovine Liver, p. 29.

4. Phospholipid Transfer Proteins in Microorganisms, p. 41; and.

5. The Non–Specific Lipid Transfer Protein (Sterol Carrier Protein 2) from Rat and Bovine Liver, p. 195.

*Primary Examiner*—Gollamudi S. Kishore
*Attorney, Agent, or Firm*—Blank Rome Comisky & McCauley LLP

[57] ABSTRACT

Active ingredient system for the lipid exchange with target structures; methods for their manufacture and their use; and products containing active ingredient systems of this type are disclosed. The active ingredient system for the transfer of lipophilic and/or amphiphilic components to target structures or from such back to the active ingredient system, as well as to their exchange with the target structures, is formed from at least one lipid component with at least one transfer protein. In the method for the manufacture of the active ingredient system, lipid and protein components are combined into systems in different configurations depending on the purpose of its use and its place of use, whereby the specificity results from the lipid used and the transfer protein employed, as well as the direction of the lipid transfer. Active ingredient systems of this type are used in technology, such as the material technology, in medicine, pharmaceuticals and in the area of cosmetology. The active ingredient system is present in products such as sprays, gels, creams or salves.

23 Claims, No Drawings

ACTIVE INGREDIENT SYSTEM AND METHOD OF MANUFACTURE THEREOF FOR TRANSFER OF LIPOPHILIC AND AMPHIPHILIC COMPONENTS TO TARGET STRUCTURES

CROSS-REFERENCE

This application is a C-I-P application of U.S. Ser. No. 07/347,026 filed May 4, 1989, now abandoned.

BACKGROUND OF THE INVENTION

1. Field of the Invention

The invention relates to an active ingredient system and more particularly to such a system for the transfer of lipophilic and/or amphiphilic components to target structures or from such target structures to the active ingredient system, as well as to the exchange thereof with such target structures, in which, to the desired degree, lipophilic and/or amphiphilic components can be transported, in order to achieve desired alteration in the composition of target structures and thus modify the characteristics thereof in accordance with specific requirements as needed.

2. Definitions

In describing the invention, the term "transfer" below will be used to describe the transport in only one direction, while the term "exchange" will be used for transport in both directions. The target structures referred to herein can be various technical systems, such as emulsions, micella, liposomes, aerosols, single layer, oligolayer, or multilayer on liquids or solid bodies, or biological systems such as lipoproteins, vesicles, organelles, bacteria, fungus, viruses, parasites, as well as pathological structures such as tumor cells, deposits in tissues, age pigments, etc.

DESCRIPTION OF THE PRIOR ART

Until now, lipid exchange between different structures has been accomplished through vesicular transport, collision, fusion or in monomeric components obtained in a medium. But these processes proceed very slowly with half-life values measured in hours, so that an efficient and targeted modification of lipid structures is generally not possible on this basis. In addition to the slow kinetics, another significant fact is that other measures, such as the one of organic solvents, detergents, high temperatures, etc., often destroy the integrity of the target structure, do not exhibit specificity and often have undesired side effects.

Neither has any technically practicable system for the rapid and targeted modification of lipid structures been made known based on the fusion of larger lipid aggregates.

A fusion system is disclosed in PCT/US85/00621 with the publication number WO 85/04880. Understood as being included within the meaning of the term fusion in the language of the art of membrane biophysics, is the fusing of two membranes. A thorough fusion results in the transfer of numerous molecules in the form of an already present membrane, which does not allow a targeted modification of the target structure at the molecular level. It is not possible with the fusion disclosed in PCT/US85/00621 to transfer molecules that cannot form membranes, such as lipid molecules. Furthermore, the membrane proteins mentioned in this reference fundamentally do not represent transfer proteins, which can be seen immediately from the fact that membrane proteins—as the name itself indicates—are located in a membrane. What is more, membranes of this type, as they are described in this reference, are inherently incapable of fulfilling a lipid transfer function because of their hydrophobic characteristics.

In a fusion system according to this reference, only membranes themselves can be used as lipid components. It is also impossible to extract individual lipid molecules through fusion.

U.S. Pat. No. 4,895,719 discloses different kinds of typical drug-carriers where the drugs are encapsulated or entrapped by liposomes. This encapsulation of drugs may be necessary where the drug is known to be rapidly eliminated (metabolized) by the body. An encapsulated drug is released continuously into the blood stream and thus can be effective over a long period of time. According to this patent these drugs can be apolipo-proteins or lung surfactant proteins. These proteins, however, are not water soluble transfer proteins which possess catalytic properties, as in the case of the present invention. The encapsulation as described in the prior art document would inhibit any catalytic efficiency of the protein and render it useless for the purposes of the present invention.

SUMMARY AND OBJECTS OF THE INVENTION

In view of the foregoing limitations and shortcomings of the prior art systems, as well as other disadvantages not specifically mentioned above, it is a primary object of the invention to provide systems for the rapidly targeted, specific and efficient lipid exchange with different target structures, in order to alter, by this means, the composition, the characteristics or the functions of the target structures.

Briefly described, the aforementioned object is accomplished according to the invention by providing an active ingredient system in which at least one lipid component, together with at least one transfer protein, form the active ingredient system. With the foregoing and other objects, advantages and features of the invention that will become hereinafter apparent the nature of the invention may be more clearly understood with reference to the following detailed description of the invention and the appended claims.

DETAILED DESCRIPTION OF THE PREFERRED EMBODIMENTS

In the active ingredient system according to the invention, a transfer is addressed that deals with a fusion based on an entirely different basic process in the area of membrane biophysics. In the active ingredient system according to the invention, a targeted modification of target structures is possible at the molecular level through the transfer of individual single molecules, for example through the lipid transfer of lipid molecules. Lipid molecules of this type, which for example cannot form a membrane themselves, cannot even be transferred by the type of fusion described earlier, but can be so transferred in the active ingredient system according to the invention. The transfer of individual lipid species to the target structures in accordance with the invention does not take place according to the laws of chance, which would result in long transfer time periods and low transfer yields due to the low number of individual lipid molecules in an aqueous medium, but rather accelerates the transfer by means of the lipid transfer system according to the invention through the use of transfer proteins. Because these proteins are components of the transfer system, they are able to act as catalysts to the transfer. The lipid transfer proteins, as found in the aqueous medium and containing the lipid components within them, transport them through the aqueous medium in order to transfer them to a target structure.

In one transfer system the lipid supply accompanying the transfer protein can be present as an emulsion, while in a fusion system, only membranes themselves can be used as lipid components. Furthermore, transfer proteins are unsuitable components for fusion processes. The transfer system according to the invention, which is based on them, is incompatible with fusion systems, both on the lipid side and on the protein side.

The lipid transfer system also allows individual molecules to be extracted.

Lipophilic or amphiphilic components, such as lecithin, sphingomyelin, cholesterin, phosphatidylserin, phosphatidylethanolamin, phosphatidylglycerol, phosphatidylinositol, ganglioside, cerebroside, fat soluble vitamins and their derivatives, triglycerides, etc., which form the active ingredient system with one or more lipid transfer proteins, are used for a transfer or an exchange with the target structures. The lipid components thereby can be present in various configurations, such as liposomes, micella, as aerosols, as emulsions, etc.

For the transfer or the exchange of the lipophilic or amphiphilic components, the active ingredient system is brought into contact with the target structure.

The advantages that can be achieved with the invention lie in the targeted alteration of structure and function of complex associations of lipophilic and amphiphilic components, such as membranes, tissues, micella, emulsions, cells, organelle, bacteria, viruses, parasites, tissue deposits, etc.

Sources for the lipophilic or amphiphilic components intended for the transfer or exchange are known to a person skilled in the art. They are either based on isolation from natural sources, such as plant or animal sources, based on chemical synthesis, or based on biotechnological methods from microbial sources.

Sources for the proteins that support the exchange or transfer of the lipid components are also known to a person skilled in the art. The proteins can be used with different specificity through isolation from natural sources such as animal tissue or through synthesis based on gene technology. The isolation can take place, for example, according to the following methods:

1. tissue disintegration
2. centrifugation
3. extraction of 100,000 g of excess
4. precipitation of accompanying proteins
   through acid
   through ammonium sulfate
5. dialysis
6. gel filtration
7. ion exchange chromatography
8. chromatofocussing.

Depending on the purpose and place of use, lipid components and protein components are combined into active ingredient systems of various configurations, whereby the specificity results from the lipid and transfer protein employed, as well as from the direction of the lipid transfer.

The following table provides an overview of possible configurations of the lipid associations:

| | Lipid Dependent | Place of Effect | Purpose of Use |
|---|---|---|---|
| Aerosols | — | Lungs, breath passages, skin, mucous membranes | Surfactant replacement to prevent drying of mucous membranes |

-continued

| | Lipid Dependent | Place of Effect | Purpose of Use |
|---|---|---|---|
| Emulsions | — | Skin, blood | Drug carrier nourishment |
| Micella | Membrane lipid, general lipid with appropriate hydrophilic and hydrophobic molecular proportions | Skin, systemic, small size (Fenestrae) | Drug carrier |
| Liposomes | Membrane lipid, general lipid with appropriate hydrophilic and hydrophobic molecular proportions | Skin, systemic, mucous membranes, such as eyes | Drug carrier membrane defects, lipid material storage, extraction of lipids |

In order to obtain lipid transfer systems as aerosols, lipids, lipid transfer proteins in an aqueous solution and additive compounds are emulsified and dispersed to form an aerosol. In order to obtain lipid transfer systems as an emulsion, additives are added to the lipid transfer proteins in aqueous solution during the emulsification of the lipids. In order to obtain the lipid transfer system as micella, the lipids are added as a pure substance to an aqueous lipid transfer protein solution.

In order to obtain lipid transfer systems as liposomes, detergent dialysis or extrusion or microemulsification as well as high pressure homogenization or ultrasonic methods are used. In detergent dialysis, the dry mixture of lipid and detergent is absorbed in an aqueous lipid transfer protein solution and the detergent is subsequently removed by dialysis.

In the extrusion method, pure lipid is absorbed in an aqueous lipid transfer protein solution and this mixture is pressed through membranes of decreasing port size.

In the microemulsification method, pure lipid is absorbed in an aqueous lipid transfer protein solution and is recirculated through an interaction chamber under high pressure.

The active ingredient system according to the invention can be obtained as follows:

A lipid transfer protein with a suitable specificity for phospholipides is isolated from tissue, particularly cattle brains. An aqueous solution of the lipid transfer protein is reacted with the suitable lipid component, such as phosphatidyl-cholin, in a quantity that is more than necessary, in terms of moles, by a factor of 5. The mixture is converted into an emulsion by a suitable technique, such as high pressure homogenization, microfluidization, etc. An aliquot part of this emulsion (relative to the protein proportion) is added to an aqueous suspension of unilamellar liposomes and the transfer activity is measured by suitable methods, such as fluorescence techniques or radioactivity. The standardized transfer system thus becomes capable of application.

The function of the lipid transfer system is based on the fact that the lipid transfer protein systems use the lipid components as donors to transfer the lipids to the various target structures. The possibility thereby exists that through a combination of certain lipid transfer proteins with corresponding lipid components, lipids can be extracted from the target structure and transferred to the lipid components. The lipid transfer protein systems in both cases assure a rapid exchange of the lipids between the lipid components and the target structure.

Lipid transfer systems of this type can be used in place of membranes. Accordingly, through a comparative analysis of the lipid proportion exchanged through the lipid transfer protein and the total lipid of a lipid membrane, an asymmetrical distribution of lipids in the bilayer can be determined. In labeling the membrane, lipids that are marked radioactively, with fluorescence and ESR or NMR labels are built into the membrane structures with the aid of the lipid transfer system.

Asymmetrical distributions of lipids can be produced in natural or artificial membrane bilayer structures through the use of lipid transfer systems. A specific composition of lipids (membrane engineering) made from natural or artificial membranes can be obtained through extraction.

In a stabilization process, lipid transfer systems with natural and artificial cells, organelles or membrane structures, such as liposomes, can be stabilized, because it eliminates membrane defects through the addition of lipids.

The active ingredient system can be used in technology to maintain or to build up a monolayer on materials, such as a sliding film, to prevent a direct aqueous wetting, or to improve the biocompatibility of boundary surfaces. In cosmetics, the active ingredient system serves to reorganize membrane structures (skin) that have been functionally damaged or altered, just as it can in dermatology.

In medicine, the active ingredient system can be used as a medication carrier (drug carrier) to stabilize liposomes relative to blood components. An additional application in medicine is that the active ingredient system is used to produce asymmetrical liposomes for a targeted application of medication (drug targeting). Especially significant is the use of the active ingredient system in handling arteriosclerosis, through which the cholesterol is extracted. For this purpose, cholesterol-free liposomes as the lipid component, are employed in connection with lipid transfer proteins.

An additional application of the active ingredient systems lies in the handling of disturbances in the lipid material exchange. Thus, for example, lipid transfer systems can be used to regulate the bile acid synthesis.

The active ingredient system can be contained in various products in technology, medicine or cosmetics. Thus, for example, the active ingredient system can be included in a salve, creme, gel or spray.

With the active ingredient system according to the invention the evaporation barrier of human and animal skin can be built up. This evaporation barrier of the skin is located in the horny stratum by a complex structure of lipid membranes. This complex structure consisting of multilamillar lipid formations can partially or totally be destroyed by different harmful influences for example by mechanical, thermal, chemical, radiological or micro-biological effects which often leads to life threatening conditions. For rebuilding under such conditions, the complex lipid structure of the evaporation barrier of the skin and the ingredient system according to the invention can be used.

An example of a lipid component which is favorably used is a glycolipid which exists in natural skin structures and which normally builds the evaporation barrier. Gluco- and galactocerebrosids are preferred glycolipids which can be isolated out of natural products or are commercially available.

The lipid component per se is not capable of building up the evaporation barrier because the necessary incorporation of the lipid components in the complex structure of the dermal evaporation barrier is too slow. However, with the active ingredient system according to the invention, a catalytic and accelerated incorporation of the lipids and the rebuilding of skin is made possible.

EXAMPLE

For such an active ingredient system the transfer protein is extracted out of cattle brain as follows:

Cattle brain is freshly homogenized and ultra-centrifugated so that 100,000 g of excess is obtained and lyophilized. The lyophilized substance is taken up in a buffer and is chromatographed against phenylsepharose. Between 20 and 30 kd of the protein fraction is recovered and further cleaned by chromatofocussing.

The thus obtained water soluble protein component(s) and the lipid component(s) are combined to create the lipid transfer system. For the synthesis of the dermal evaporation barrier the active ingredient system is used, for example, as a liposomal hydrogel.

The incorporation of the lipid component(s) in the target structure—in this case in the form of a membrane—is enhanced by a factor of 100 to 1000, if the active ingredient system according to the invention is used compared to the use of only the lipid component(s), as a rebuild substance for the evaporation barrier of natural skin.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for applying a lipid to the lung surface and surfaces of the oronasal passages comprising, selecting a lipid to apply to the lung surface or surface of the oronasal passages, selecting a lipid transfer protein or mixture of lipid transfer proteins that can transfer the selected lipid, forming an active ingredient system by combining an aqueous solution of said lipid transfer protein with said lipid and applying said active ingredient system to the surface of the lung and oronasal passages.

2. The method of claim 1, wherein the active ingredient system is in a form selected from the group consisting of emulsions, micelles, liposomes and aerosols.

3. The method of claim 1, wherein the lipid is selected from a phospholipid.

4. The method of claim 3, wherein the phospholipid is selected from the group consisting of lecithin, phosphatidylserine, phosphatidylglycerol, phosphatidylethanolamine, and phosphatidylinositol.

5. The method of claim 1, wherein the lipid is selected from a glycolipid.

6. The method of claim 5, wherein the glycolipid is selected from the group consisting of sphingomylin, ganglio sides, glucocerebrosides and galactocerebrosides.

7. The method of claim 1, wherein the lipid is selected from a fat soluable vitamin.

8. The method of claim 7, wherein the fat soluable vitamin is selected from the group consisting of vitamins A, D, E, and K.

9. The method of claim 1, wherein the lipid is selected from the group consisting of cholesterol, cholesterol esters, triglycerides and steroids.

10. The method of claim 1, further comprising the selection and addition of a lipophilic drug to said lipid.

11. A method for applying a lipid to the skin's surface comprising, selecting a lipid to apply onto the lipid layer of the skin, selecting a lipid transfer protein or mixture of lipid transfer proteins that can transfer the selected lipid, forming an active ingredient system by combining an aqueous solution of said lipid and topically applying said active ingredient system to the skin.

12. The method of claim 11, wherein the active ingredient system is in the form selected from the group consisting of emulsions, micelles, liposomes and areosols.

13. The method of claim 11, wherein the lipid is selected from a fat soluble vitamin.

14. The method of claim 13, wherein the fat soluble vitamin is selected from the group consisting of vitamins A, D, E, and K.

15. The method of claim 13 wherein the fat soluble vitamin is α-D-tocopherol.

16. The method of claim 11, wherein the lipid is selected from a phospholipid.

17. The method of claim 16, wherein the phospholipid is selected from the group consisting of lecithin, phosphatidylserine, phosphatidylglycerol, phosphatidylethanolamine, and phosphatidylinositol.

18. The method of claim 11, wherein the lipid is selected from a glycolipid.

19. The method of claim 18, wherein the glycolipid is selected from the group consisting of sphingomylin, gangliosides, glucocerebrosides and galactocerebrosides.

20. The method of claim 11, wherein the lipid is selected from the group consisting of cholesterol, cholesterol esters, triglycerides and steroids.

21. The method of claim 11, further comprising the selection and addition of a lipophilic drug to said lipid.

22. The method of claim 1, wherein the lipid is a carotenoid.

23. The method of claim 11 wherein the lipid is a carotenoid.

* * * * *